(12) United States Patent
Armoundas et al.

(10) Patent No.: US 8,565,876 B2
(45) Date of Patent: *Oct. 22, 2013

(54) METHOD AND APPARATUS FOR TREATMENT OF CARDIAC TACHYARRHYTHMIAS

(75) Inventors: Antonis A. Armoundas, Lincoln, MA (US); Richard J. Cohen, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/492,191

(22) Filed: Jun. 8, 2012

(65) Prior Publication Data

US 2013/0013013 A1 Jan. 10, 2013

Related U.S. Application Data

(63) Continuation of application No. 11/493,466, filed on Jul. 26, 2006, now Pat. No. 8,249,704, which is a continuation-in-part of application No. 10/299,415, filed on Nov. 19, 2002, now Pat. No. 7,336,995.

(51) Int. Cl.
*A61N 1/00* (2006.01)
(52) U.S. Cl.
USPC ............................................. 607/14; 607/25
(58) Field of Classification Search
USPC .................................................... 607/4–28
See application file for complete search history.

(56) References Cited

U.S. PATENT DOCUMENTS

| | | |
|---|---|---|
| 5,749,900 A | 5/1998 | Schroeppel et al. |
| 5,842,997 A | 12/1998 | Verrier et al. |
| 5,921,940 A | 7/1999 | Verrier et al. |
| 6,058,328 A | 5/2000 | Levine et al. |
| 6,129,678 A | 10/2000 | Ryan et al. |
| 6,253,107 B1 | 6/2001 | Albrecht et al. |
| 6,317,631 B1 | 11/2001 | Ben-Haim et al. |
| 6,438,409 B1 | 8/2002 | Malik et al. |
| 7,096,064 B2 | 8/2006 | Deno et al. |
| 2002/0138106 A1 | 9/2002 | Christini et al. |
| 2004/0002743 A1 | 1/2004 | Park et al. |
| 2004/0049235 A1 | 3/2004 | Deno et al. |

FOREIGN PATENT DOCUMENTS

WO   WO-02/34123 A2   5/2002

OTHER PUBLICATIONS

Adam, et al., "Fluctuations in T-wave morphology and susceptibility to ventricular fibrillation", J. Electrocardiol, 17: 209-18, 1984.
Adam, et al., "Ventricular fibrillation and fluctuations in the magnitude of the repolarization vector", IEEE Computers Cardiol., 241-244, 1982.
Adamson, et al., "Electrophysiology TfotEsocatNASoPa. Heart rate variability, standards of measurement, physiological interpretation and clinical use", Circulation, 93: 1043-1065, 1996.

(Continued)

*Primary Examiner* — Scott Getzow
(74) *Attorney, Agent, or Firm* — Choate, Hall & Stewart LLP; Brenda H. Jarrell; Daniel S. Matthews

(57) ABSTRACT

Method and apparatus for preventing heart rhythm disturbances by recording cardiac electrical activity, measuring beat-to-beat variability in the morphology of electrocardiographic waveforms, and using the measured beat-to-beat variability to control the delivery of electrical impulses to the heart during the absolute refractory period.

19 Claims, 5 Drawing Sheets

(56) References Cited

OTHER PUBLICATIONS

Adamson, et al., "Unexpected interaction between beta-adrenergic blockade and heart rate variability before and after myocardial infarction. A longitudinal study in dogs at high and low risk for sudden death", Circulation, 90: 976-82, 1994.

Armoundas, et al. "A stochastic nonlinear autoregressive algorithm reflects nonlinear dynamics of heart-rate fluctuations", Ann. Biomed. Eng., 30: 192-201, 2002.

Armoundas, et al., "Images in cardiovascular medicine. T-wave alternans preceding torsade de pointes ventricular tachycardia", Circulation, 101: 2550, 2000.

Augello, et al., "Cardiac contractility modulation by non-excitatory electrical currents. The new frontier for electrical therapy of heart failure", Ital Heart J., 5 Suppl 6: 68S-75S, 2004.

Bigger, et al., "Frequency domain measures of heart period variability and mortality after myocardial infarction", Circulation, 85: 164-71, 1992.

Bigger, et al., "Predicting mortality after myocardial infarction from the response of RR variability to antiarrhythmic drug therapy", J. Am. Coll. Cardiol., 23: 733-40, 1994.

Brunckhorst, et al., "Cardiac contractility modulation by non-excitatory currents: studies in isolated cardiac muscle", Eur J Heart Fail., 8(1): 7-15, 2006.

Buxton, et al., "Electrophysiologic testing to identify patients with coronary artery disease who are at risk for sudden death—Multicenter Unsustained Tachycardia Trial Investigators", N. Engl. J. Med., 342: 1937-45, 2000.

Buxton, et al., "Electrophysiologic Testing to Identify Patients with Coronary Artery Disease Who Are at Risk for Sudden Death," The New England Journal of Medicine, 342: 1937-45, 2000.

Buxton, et al., "Nonsustained ventricular tachycardia", Cardiol. Clin., 18: 327-36, 2000.

Calabrese, et al., "ST-T segment alternans in ventricular tachycardia associated with inversion of the U wave in Prinzmetal angina during exercise test. Description of a clinical case", G. Ital. Cardiol., 20: 239-41, 1990.

Cheema, et al., "Nonsustained Ventricular Tachycardia in the Setting of Acute Myocardial Infarction: Tachycardia Characteristics and Their Prognostic Implications," Circulation, 98: 2030-2036, 1998.

Cheng, "Electrical alternans. An association with coronary artery spasm", Arch. Intern. Med., 143: 1052-3, 1983.

Chon, et al. "Detection of "noisy" chaos in a time series", Methods Inf Med., 36: 294-7, 1997.

Chon, et al., "Detection of Chaotic Determinism in Time Series from Randomly Forced Maps," Biosignal Interpretation, 103-106, 1997.

Chon, et al., "Modeling nonlinear determinism in short time series from noise driven discrete and continuous systems", Int. J. Bifurcation & Chaos, 10: 2745-2766, 2000.

Cinca, et al., "The dependence of T wave alternans on diastolic resting period duration", Eur. J. Cardiol., 7: 299-309, 1978.

Clancy, et al., "A simple electrical-mechanical model of the heart applied to the study of electrical-mechanical alternans", IEEE Trans Biomed Eng, 38: 551-60, 1991.

Costello, et al., "Echocardiographic examination in left ventricular alternans", Chest, 75: 72-5, 1979.

Dilly, et al., "Changes in monophasic action potential duration during the first hour of regional myocardial ischaemia in the anaesthetised pig", Cardiovasc Res, 21: 908-15, 1987.

Dilly, et al., "Electrophysiological alternans and restitution during acute regional ischaemia in myocardium of anaesthetized pig", J Physiol (London), 402: 315-33, 1988.

European Application No. 07813216.4, Supplementary European Search Report, Sep. 21, 2010.

Fallen, et al., "Spectral analysis of heart rate variability following human heart transplantation: evidence for functional reinnervation", J. Auton. Nerv. Syst., 23: 199-206, 1988.

Final Office Action dated Mar. 7, 2006, pertaining to U.S. Appl. No. 10/299,415, 4 pages.

Final Office Action dated May 21, 2007, pertaining to U.S. Appl. No. 10/299,415, 4 pages.

Fisch, et al., "T wave alternans: an association with abrupt rate change", Am. Heart J., 81: 817-21, 1971.

Grassberger, et al., "Measuring the strangeness of strange attractors", Physica D., 9: 183-208, 1983.

H.H., et al., "Electrical alternans", NY State J Med, 1: 1164-1166, 1948.

Hashimoto, et al., "Effects of calcium antagonists on the alternation of the ST-T complex and associated conduction abnormalities during coronary occlusion in dogs", Br. J. Pharmacol., 74: 371-80, 1981.

Hashimoto, et al., "Potentiating effects of a ventricular premature beat on the alternation of the ST-T complex of epicardial electrograms and the incidence of ventricular arrhythmias during acute coronary occlusion in dogs", J. Electrocardiol., 17: 289-301, 1984.

Huikuri, et al., "Power-law relationship of heart rate variability as a predictor of mortality in the elderly", Circulation, 97: 2031-6, 1998.

International Preliminary Report on Patentability for PCT/US2007/074098, issued Jan. 27, 2009.

International Search Report for PCT/US2007/074098, issued Jul. 7, 2008.

Kanters, et al., "Lack of evidence for low-dimensional chaos in heart rate variability", J Cardiovasc Electrophysiol, 5: 591-601, 1994.

Kanters, et al., "Short- and long-term variations in non-linear dynamics of heart rate variability", Cardiovasc. Res., 31: 400-9, 1996.

Kaufman, et al., "Influence of heart rate and sympathetic stimulation on arrhythmogenic T wave alternans", Am. J. Physiol. Heart Circ. Physiol., 279: H1248-55, 2000.

Kleiger, et al., "Decreased heart rate variability and its association with increased mortality after acute myocardial infarction", Am. J. Cardiol., 59: 256-62, 1987.

Kleinfeld, et al., "Alternans of the ST segment in Prinzmetal's angina", Circulation, 55: 574-7, 1977.

Kleinfeld, et al., "Pacemaker alternans: a review", Pacing Clin. Electrophysiol., 10: 924-33, 1987.

Konta, et al., "Significance of discordant ST alternans in ventricular fibrillation", Circulation, 82: 2185-9, 1990.

Lewis, "Notes upon alternation of the heart", Q J Med, 4: 141-144, 1910.

Malik, et al., "Heart rate variability in relation to prognosis after myocardial infarction: selection of optimal processing techniques", Eur. Heart J., 10: 1060-74, 1989.

Malik, et al., "Heart rate variability, standards of measurement, physiological interpretation and clinical use," Circulation, 93: 1043-1065, 1996.

Malik, et al., "Influence of the recognition artefact in automatic analysis of long-term electrocardiograms on time-domain measurement of heart rate variability", Med. Biol. Eng. Comput., 31: 539-44, 1993.

Nearing, et al., "Dynamic tracking of cardiac vulnerability by complex demodulation of the T wave", Science, 252: 437-40, 1991.

Nearing, et al., "Personal computer system for tracking cardiac vulnerability by complex demodulation of the T wave", J. Appl. Physiol., 74: 2606-12, 1993.

Nearing, et al., "Potent antifibrillatory effect of combined blockade of calcium channels and 5-HT2 receptors with nexopamil during myocardial ischemia and reperfusion in dogs: comparison to diltiazem", J. Cardiovasc. Pharmacol., 27: 777-87, 1996.

Nearing, et al., "Quantification of ischaemia induced vulnerability by precordial T wave alternans analysis in dog and human", Cardiovasc. Res., 28: 1440-9, 1994.

Non-Final Office Action dated Jul. 8, 2005, pertaining to U.S. Appl. No. 10/299,415, 4 pages.

Non-Final Office Action dated Sep. 22, 2006, pertaining to U.S. Appl. No. 10/299,415, 4 pages.

Pappone, et al., "Cardiac contractility modulation by electric currents applied during the refractory period in patients with heart failure secondary to ischemic or idiopathic dilated cardiomyopathy", Am J Cardiol., 90(12): 1307-1313, 2002.

Pappone, et al., "Electrical modulation of cardiac contractility: clinical aspects in congestive heart failure", Heart Fail Rev., 6(1): 55-60, 2001.

(56) References Cited

OTHER PUBLICATIONS

Pappone, et al., "First human chronic experience with cardiac contractility modulation by nonexcitatory electrical currents for treating systolic heart failure: mid-term safety and efficacy results from a multicenter study", J Cardiovasc Electrophysiol., 15(4): 418-427, 2004.

Platt, et al., "Occult T wave alternans in long QT syndrome", J. Cardiovasc. Electrophysiol., 7: 144-8, 1996.

Prystowsky, "Screening and therapy for patients with nonsustained ventricular tachycardia", Am. J. Cardiol., 86: K34-K39, 2000.

Puletti, et al., "Alternans of the ST segment and T wave in acute myocardial infarction", J. Electrocardiol., 13: 297-300, 1980.

Reddy, et al., "Repolarization alternans associated with alcoholism and hypomagnesemia", Am. J. Cardiol., 53: 390-391, 1984.

Ritzenberg et al., "Period multupling-evidence for nonlinear behaviour of the canine heart", Nature, 307: 159-61, 1984.

Rosenbaum, et al., "Electrical alternans and vulnerability to ventricular arrhythmias", N. Engl. J. Med., 330: 235-41, 1994.

Rosenbaum, et al., "Predicting sudden cardiac death from T wave alternans of the surface electrocardiogram: promise and pitfalls", J. Cardiovasc. Electrophysiol., 7: 1095-111, 1996.

Salerno, et al., "Ventricular arrhythmias during acute myocardial ischaemia in man. The role and significance of R-ST-T alternans and the prevention of ischaemic sudden death by medical treatment", Eur Heart J, 7 Suppl A: 63-75, 1986.

Schmidt, et al., "Nonlinear methods for heart rate variability", Heart Rate Variability., 87-98, 1995.

Schwartz, et al., "Electrical alternation of the T-wave: clinical and experimental evidence of its relationship with the sympathetic nervous system and with the long Q-T syndrome", Am. Heart J., 89: 45-50, 1975.

Shimoni, et al., "Electrical alternans of giant U waves with multiple electrolyte deficits", Am. J. Cardiol., 54: 920-1, 1984.

Shinbrot, et al., "Using chaos to direct trajectories to targets", Physical Review Letters., 65(26): 3215-3218, 1990.

Smith, and Cohen, "Simple finite-element model accounts for wide range of cardiac dysrhythmias", Proc Natl Acad Sci, 81: 233-7, 1984.

Smith, et al., "Electrical alternans and cardiac electrical instability", Circulation, 77: 110-21, 1988.

Stevenson, et al., "Prevention of Sudden Death in Heart Failure", J. Cardiovasc Electrophysiol, 12: 112-4, 2001.

Sutton, et al., Eur. Heart J. 12: 70, 1991.

Tovar, et al., "Electrophysiological Deterioration During Long-Duration Ventricular Fibrillation", Circulation, 102: 2886-91, 2000.

Verrier, et al., "Electrophysiologic basis for T wave alternans as an index of vulnerability to ventricular fibrillation", J. Cardiovasc. Electrophysiol., 5: 445-61, 1994.

Verrier, et al., "Life-threatening cardiovascular consequences of anger in patients with coronary heart disease", Cardiol. Clin., 14: 289-307, 1996.

Wolf, et al., "Sinus arrhythmia in acute myocardial infarction", Med. J. Aust., 2: 52-3, 1978.

Written Opinion for PCT/US2007/074098, issued Jul. 7, 2008.

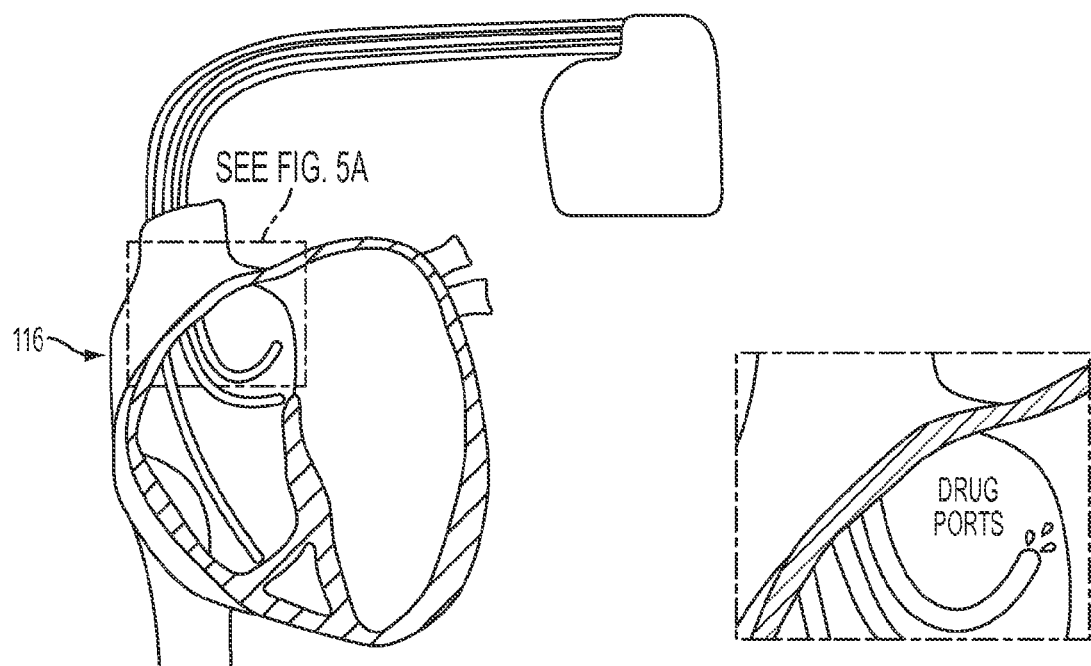

ized that use of implantable cardioverter defibrillators has reduced the incidence of SCD in high risk patients.

METHOD AND APPARATUS FOR TREATMENT OF CARDIAC TACHYARRHYTHMIAS

CROSS-REFERENCE TO RELATED APPLICATIONS

This application is a continuation of U.S. patent application Ser. No. 11/493,466, filed on Jul. 26, 2006, which is a continuation-in-part of application Ser. No. 10/299,415, filed Nov. 19, 2002, the contents of each of which are incorporated herein by reference in their entirety.

FIELD OF THE INVENTION

The present invention relates to methods and apparatus for preventing an adverse clinical event. The adverse clinical event includes, but is not limited to, adverse cardiovascular events such as occurrences of serious heart rhythm disturbances such as ventricular fibrillation, tachyarrhythmia, bradyarrhythmia, myocardial infarction, sudden cardiac death, and related maladies such as loss of consciousness, development of diminished cerebral function. The risk of the adverse clinical event is determined through electrocardiogram analysis.

BACKGROUND OF THE INVENTION

Cardiovascular disease is the greatest cause of morbidity and mortality in the industrialized world. It not only strikes down a significant fraction of the population without warning but also causes prolonged suffering and disability in an even larger number. Sudden cardiac death (SCD) is prevalent in the population, however it is difficult to treat because it is difficult to predict in which individuals it will occur, and it often occurs without warning, in an out of a hospital setting. It is widely acknowledged that use of implantable cardioverter defibrillators has reduced the incidence of SCD in high risk patients.

With reference to FIGS. 1a and 1b, an implantable cardioverter defibrillator (ICD) 100 is an implantable device that detects the initiation of arrhythmias, such as ventricular tachycardia or fibrillation, and terminates them by delivery of one or more electrical impulses to the heart 102. Often the energy of these impulses is quite large compared to the energy of impulses delivered by an artificial pacemaker, which is used to pace the heart but not to terminate arrhythmias. The increased ease of ICD implantation as well as advances in ICD technology has led to a rapid growth in the rate of ICD implantation. However, ICDs generally are used to terminate an arrhythmia, such as ventricular tachycardia or fibrillation, only after the arrhythmia has started. This feature of ICD function may lead to patients losing consciousness once the arrhythmia starts and also leads to patients experiencing what may be very uncomfortable electrical discharges of the ICD. Frequent ICD discharge can lead to extreme psychological stress in many patients. Some patients have an ICD placed, only to suffer recurrent shocks and finally to have the device deactivated. (Stevenson W. G., et al., "Prevention of Sudden Death in Heart Failure", *J. Cardiovasc Electrophysiol* 2001; 12:112-4. The contents of this article and all articles cited below are hereby incorporated by reference into the present application as if reproduced in their entireties.) Recently, it was shown that a rapid and progressive electrophysiological deterioration during ventricular fibrillation that may explain the decreased probability of successful resuscitation after prolonged fibrillation. (Tovar O. H., et al., "Electrophysiological Deterioration During Long-Duration Ventricular Fibrillation", *Circulation* 2000; 102:2886-91) Also, the more often the ICD discharges, the shorter is the life of its battery. Frequent ICD discharge can also damage the heart tissue itself and as a result may make the heart more susceptible to future arrhythmias. Thus it would be highly desirable to be able to be able to prevent arrhythmias from starting rather than terminating them after their initiation by administration of an electrical shock.

Arrhythmias such as ventricular tachycardia and fibrillation are often caused by an electrical mechanism called reentry. With reference to FIGS. 2A-2D, reentry involves a loop-like path of electrical activation 104 circulating through a region of heart tissue, re-entering regions 106 that had been previously activated in prior loops. In early ischemic arrhythmias, ventricular tachycardia and fibrillation have been shown to depend on reentrant excitation. Although reentrant excitation is thought to underlie a variety of benign and malignant cardiac rhythms, descriptions of the mechanisms that are involved in the development of reentry remain obscured. A major factor leading to the genesis of ventricular fibrillation during ischemia is dispersion of refractoriness. Dispersion of refractoriness is a measure of non-homogeneous recovery of excitability in a given mass of cardiac tissue (tissue is called refractory when it can not be re-stimulated until it has recovered). In normal myocardium the excitability is strictly proportional to the duration of repolarization. Reentry is the most likely mechanism of arrhythmia facilitated by enhanced dispersion of repolarization. The elements that are most often represented in the experimental or clinical models of arrhythmias attributed to reentry include non-uniform conduction, non-uniform excitability, and non-uniform refractoriness.

Ischemia alters refractoriness through its effects on resting potential and action potential duration. These effects are non-uniform during regional ischemia because of local variations in blood flow and diffusion of substrate and metabolites across the ischemic boundary. The resulting non-uniformity in refractoriness undoubtedly contributes to the increased vulnerability of an ischemic heart to fibrillation. An important mechanism for enhancing dispersion of refractory period is alternation of the action potential from beat to beat.

Action potential alternans involves an alternating sequence in which the shape of the action potential (the wave-like pattern of variation of a cell's transmembrane potential) associated with an individual cardiac cell changes on an every other beat basis (as shown in FIG. 3 between beat 108 and beat 110). If the duration of the action potential alternates on an every other beat basis, then the duration of refractory period also alternates in duration because the refractory period is generally roughly comparable to the duration of the action potential. Thus action potential alternans creates a situation in which a region of the myocardium has a long refractory period on an every other beat basis. On these alternate beats, a region with action potential alternans can create islands of refractory tissue that can cause fractionation of activation wavefronts. Thus, action potential alternans, which generally occurs in diseased tissue, can promote the development of reentry.

The presence of action potential alternans can be detected in an electrocardiogram as ST segment and/or T-wave alternans (repolarization alternans—see representative portions 112 and 114 of heart beats depicted in FIG. 4). In the surface electrocardiogram (ECG), repolarization alternans, has been correlated with the presence of ventricular vulnerability to arrhythmias in humans. In this application, we define repolarization alternans to be any change in the morphology of the ST segment or T-wave of the electrocardiogram occurring on an every other beat basis.

Computer simulations of cardiac conduction processes in the inventors' laboratory predicted the relationship between the presence of electrical alternans and enhanced susceptibility to the onset of reentrant rhythm disturbances. (Smith, J. M., Cohen, R. J., "Simple finite-element model accounts for wide range of cardiac dysrhythmias", *Proc Natl Acad Sci* 1984; 81:233-7.)

Specifically, the simulated ECGs have shown electrical alternans in myocardial cells that have refractory periods that exceed a threshold cycle length and as a result there will be a corresponding subpopulation of cells that can be at most be activated every second beat. This is reflected in electrical alternans in the ECG illustrated in FIG. 4. This process leads to wave-front fractionation thus being the predisposing factor to reentrant ventricular dysrhythmias.

Electrical alternans have been shown to precede ventricular fibrillation in dogs. (Smith, J M, et al., "Electrical alternans and cardiac electrical instability", *Circulation* 1988, 77:110-21; Nearing, B D, et al., "Dynamic tracking of cardiac vulnerability by complex demodulation of the T wave", *Science* 1991, 252:437-40.) A computer algorithm developed by the inventors that is sensitive to microvolt level oscillations of the surface ECG, in a series of animal experiments, revealed that coronary artery occlusion was also uniformly accompanied by a decrease in electrical stability (as measured by the ventricular fibrillation threshold) and occlusion was frequently accompanied by an increase in the observed alternation in ECG vector morphology. A description of the algorithm, which may be employed in the present invention for estimating repolarization alternans, and the noted results may be found in the following references: Smith, J. M., and Cohen, R. J., "Simple finite-element model accounts for wide range of cardiac dysrhythmias", *Proc Natl Acad Sci USA* 1984, 81:233-7; Adam, D. R., et al., "Fluctuations in T-wave morphology and susceptibility to ventricular fibrillation", *J. Electrocardiol* 1984, 17:209-18; and Clancy, E. A., et al., "A simple electrical-mechanical model of the heart applied to the study of electrical-mechanical alternans", *IEEE Trans Biomed Eng* 1991, 38:551-60.

In humans, alternation in electrical repolarization processes in the heart has been associated with increased vulnerability to ventricular arrhythmias under diverse pathophysiologic conditions such as myocardial ischemia (See Dilly, S. G., et al., "Electrophysiological alternans and restitution during acute regional ischaemia in myocardium of anaesthetized pig", *J Physiol* (London) 1988, 402:315-33; Dilly, S. G., et al., "Changes in monophasic action potential duration during the first hour of regional myocardial ischaemia in the anaesthetised pig", *Cardiovasc Res* 1987, 21:908-15; Lewis, T., "Notes upon alternation of the heart", *Q J Med* 1910, 4:141-144; Salerno, J. A., et al., "Ventricular arrhythmias during acute myocardial ischaemia in man. The role and significance of R-ST-T alternans and the prevention of ischaemic sudden death by medical treatment", *Eur Heart J* 1986, 7 Suppl A:63-75.), Prinzmetal's angina (See Kleinfeld, M. J., et al., "Alternans of the ST segment in Prinzmetal's angina", *Circulation,* 1977, 55:574-7; Reddy, C. V., et al., "Repolarization alternans associated with alcoholism and hypomagnesemia", *Am. J. Cardiol.,* 1984, 53:390-1), altered autonomic state (See Nearing, B. D., et al., "Potent antifibrillatory effect of combined blockade of calcium channels and 5-HT2 receptors with nexopamil during myocardial ischemia and reperfusion in dogs: comparison to diltiazem", *J. Cardiovasc. Pharmacol.,* 1996, 27:777-87; Cheng, T. C., "Electrical alternans. An association with coronary artery spasm", *Arch. Intern. Med.,* 1983, 143:1052-3; Kaufman, E. S., et al., "Influence of heart rate and sympathetic stimulation on arrhythmogenic T wave alternans", *Am. J. Physiol. Heart Circ. Physiol.* 2000; 279: H1248-55), electrolyte abnormalities (See Reddy; Kaufman; Shimoni, Z, et al., "Electrical alternans of giant U waves with multiple electrolyte deficits", *Am. J. Cardiol.* 1984, 54:920-1), and the long QT syndrome (See Schwartz, P. J., et al., "Electrical alternation of the T-wave: clinical and experimental evidence of its relationship with the sympathetic nervous system and with the long Q-T syndrome", *Am. Heart. J.,* 1975, 89:45-50; Platt, S. B., et al., "Occult T wave alternans in long QT syndrome", *J. Cardiovasc. Electrophysiol.,* 1996, 7:144-8; Armoundas, A. A., et al., "Images in cardiovascular medicine. T-wave alternans preceding torsade de pointes ventricular tachycardia", *Circulation,* 2000, 101:2550). Repolarization alternans in the form of macroscopically visible TWA has been associated anecdotally with a variety of conditions associated with an increased risk of ventricular arrhythmias (See H. H., et al., "Electrical alternans", *NY State J Med* 1948, 1:1164-1166; Kleinfeld, M, et al., "Pacemaker alternans: a review", *Pacing Clin. Electrophysiol.,* 1987, 10:924-33; Calabrese, G, et al., "ST-T segment alternans in ventricular tachycardia associated with inversion of the U wave in Prinzmetal angina during exercise test. Description of a clinical case", *G. Ital. Cardiol.,* 1990, 20:239-41; Cinca, J, et al., "The dependence of T wave alternans on diastolic resting period duration", *Eur. J. Cardiol.,* 1978, 7:299-309; Costello, D L, et al., "Echocardiographic examination in left ventricular alternans", *Chest,* 1979, 75:72-5; Fisch, C, et al., "T wave alternans: an association with abrupt rate change", *Am. Heart* 1, 1971, 81:817-21; Hashimoto, H, et al., "Potentiating effects of a ventricular premature beat on the alternation of the ST-T complex of epicardial electrograms and the incidence of ventricular arrhythmias during acute coronary occlusion in dogs", *J. Electrocardiol.,* 1984, 17:289-301; Hashimoto, H, et al., "Effects of calcium antagonists on the alternation of the ST-T complex and associated conduction abnormalities during coronary occlusion in dogs", *Br. J. Pharmacol.,* 1981, 74:371-80; Konta, T, et al., "Significance of discordant ST alternans in ventricular fibrillation", *Circulation,* 1990, 82:2185-9; Puletti, M, et al., "Alternans of the ST segment and T wave in acute myocardial infarction", *J. Electrocardiol.,* 1980, 13:297-300.

Microvolt level T-wave alternans was first reported in 1982. (See Adam, D. R., et al., "Ventricular fibrillation and fluctuations in the magnitude of the repolarization vector", *IEEE Computers Cardiol.,* 1982, 241-244.) Subsequently, a series of studies led to the development of a spectral method to detect subtle microvolt level repolarization alternans, and developed a relationship between alternans and ventricular fibrillation thresholds in animal studies and susceptibility to ventricular arrhythmias in humans undergoing EPS testing. (See Smith; Adam; Ritzenberg, A. L., et al., "Period multupling-evidence for nonlinear behaviour of the canine heart", *Nature,* 1984, 307:159-61.) These studies experimentally linked repolarization alternans to increased susceptibility to ventricular tachyarrhythmias.

Recent studies have demonstrated that the presence of microvolt level repolarization alternans (generally not visible upon visual inspection of the electrocardiogram, but detectable using advanced signal processing techniques such as described in: Smith; Clancy; Platt; Rosenbaum, D. S., et al., "Electrical alternans and vulnerability to ventricular arrhythmias", *N. Engl. J. Med.,* 1994, 330:235-41; and Rosenbaum, D. S., et al., "Predicting sudden cardiac death from T wave alternans of the surface electrocardiogram: promise and pitfalls", *J. Cardiovasc. Electrophysiol.,* 1996, 7:1095-111), is associated with an increased risk of ventricular arrhythmias and sudden cardiac death. (See Verrier, R. L., et al., "Electrophysiologic basis for T wave alternans as an index of vulnerability to ventricular fibrillation", *J. Cardiovasc. Electrophysiol.,* 1994, 5:445-61; Verrier, R. L., et al., "Life-threatening cardiovascular consequences of anger in patients with coronary heart disease", *Cardiol. Clin.,* 1996, 14:289-307; Nearing, B. D., et al., "Personal computer system for tracking cardiac vulnerability by complex demodulation of the T wave", *J. Appl. Physiol.,* 1993, 74:2606-12; and Nearing, B. D., et al., "Quantification of ischaemia induced vulnerability by precordial T wave alternans analysis in dog and human", *Cardiovasc. Res.,* 1994, 28:1440-9).

In ECG tracings obtained from Holter monitoring, there has been evidence that repolarization alternans persist for long periods before the onset of an unstable heart rhythm like ventricular tachycardia or ventricular fibrillation (See Armoundas, A. et al., "Images in cardiovascular medicine. T-wave alternans preceding torsade de pointes ventricular tachycardia", *Circulation* 2000; 101:2550.)

Thus, in both computer simulations and experimental reports electrical alternans has been shown to increase its magnitude in the stage preceding a malignant heart rhythm like ventricular fibrillation.

From the time heart rate variability (HRV) was first appreciated as a harbinger of sudden cardiac death in post myocardial infarction patients by Wolf et al. (Wolf, M. M., et al., "Sinus arrhythmia in acute myocardial infarction", *Med. J. Aust.* 1978, 2:52-3), numerous studies have established a significant relationship between HRV and susceptibility to lethal ventricular arrhythmias. (See Kleiger, R. E., et al., "Decreased heart rate variability and its association with increased mortality after acute myocardial infarction", *Am. J. Cardiol.,* 1987, 59:256-62; Malik, M, et al., "Heart rate variability in relation to prognosis after myocardial infarction: selection of optimal processing techniques", *Eur. Heart J.,* 1989, 10:1060-74; Bigger, J. T., et al., "Frequency domain measures of heart period variability and mortality after myocardial infarction", *Circulation,* 1992, 85:164-71; and Fallen, E. L., et al., "Spectral analysis of heart rate variability following human heart transplantation: evidence for functional reinnervation", *J. Auton. Nerv. Syst.,* 1988, 23:199-206.) A major issue has been how to describe HRV mathematically. The phenomenon of fluctuations in the interval between consecutive heart beats has been the subject of investigations using a wide range of methodologies including time domain (See Adamson, P. B., et al., "Unexpected interaction between beta-adrenergic blockade and heart rate variability before and after myocardial infarction. A longitudinal study in dogs at high and low risk for sudden death", *Circulation,* 1994, 90:976-82; and "Electrophysiology TfotEsocatNASoPa. Heart rate variability, standards of measurement, physiological interpretation and clinical use", *Circulation,* 1996, 93:1043-1065), frequency domain (See Bigger, J. T., et al., "Predicting mortality after myocardial infarction from the response of RR variability to antiarrhythmic drug therapy", *J. Am. Coll. Cardiol.,* 1994, 23:733-40; and Huikuri, H. V., et al., "Power-law relationship of heart rate variability as a predictor of mortality in the elderly", *Circulation,* 1998, 97:2031-6), geometric (Malik, M, et al., "Influence of the recognition artefact in automatic analysis of long-term electrocardiograms on time-domain measurement of heart rate variability", *Med. Biol. Eng. Comput.,* 1993, 31:539-44), and non-linear (See Schmidt, G, et al., "Nonlinear methods for heart rate variability", In: Malik M, Camm A J, eds. *Heart Rate Variability.* Armonk, N.Y.: Futura, 1995:87-98; Kanters, J. K., et al., "Short- and long-term variations in non-linear dynamics of heart rate variability", *Cardiovasc. Res.,* 1996, 31:400-9; and Kanters, J. K., et al., "Lack of evidence for low-dimensional chaos in heart rate variability. J Cardiovasc Electrophysiol 1994; 5:591-601), methods. With the general recognition of nonlinear dynamics theory in the mid 80's, it was proposed that HRV should be viewed as the result of nonlinear determinism in the regulatory systems governing the heart rate. Parameters indicative of possible low-dimensional nonlinear determinism include Lyapunov exponents, strange attractors and correlation dimensions (Grassberger, P, et al., "Measuring the strangeness of strange attractors", *Physica D.,* 1983, 9:183-208). For example, it has been suggested that the correlation dimension (CD) could be used to distinguish patients who develop ventricular fibrillation during the monitoring period from those who do not. (See Chon, K. H., et al., "Modeling nonlinear determinism in short time series from noise driven discrete and continuous systems", *Int. J. Bifurcation & Chaos,* 2000, 10:2745-2766.)

While ICDs currently are an effective therapy for the termination of heart rhythm disturbances (See Prystowsky, E. N., "Screening and therapy for patients with nonsustained ventricular tachycardia", *Am. J. Cardiol.,* 2000, 86:K34-K39; Buxton, A. E., et al., "Nonsustained ventricular tachycardia", *Cardiol. Clin.,* 2000, 18:327-36, viii; and Buxton, A. E., et al., "Electrophysiologic testing to identify patients with coronary artery disease who are at risk for sudden death—Multicenter Unsustained Tachycardia Trial Investigators", *N. Engl. J. Med.,* 2000, 342:1937-45), their role is to deliver electrical impulses to terminate the arrhythmia rather than to prevent its onset. Thus, patients are being subjected to a serious arrhythmia for a period of time until therapy is delivered. Also, delivery of electrical impulses from the ICD may be painful and may damage the heart.

There remains, therefore, a need to prevent arrhythmias from initiating rather than treating them with what may be much higher energy electrical pulses after the arrhythmias have been initiated.

A key question underlying the control of alternans is to design perturbations that stabilize the system about one of the unstable equilibrium states of the system (Shinbrot T, Ott E, Grebogi C, et al. Using chaos to direct trajectories to targets. *Physical Review Letters.* Dec. 24, 1990; 65(26):3215-3218). The corresponding unstable equilibrium state is a 1:1 (period 1) pattern, for which the local APD is the same for each stimulus. That is, by making small real-time adjustments to the pacing interval, based on measurements of the APD or the QT interval if it refers to adjustments of the whole heart, one should be able to achieve this state. One approach that has been applied successfully in predictably controlling the APD (shortening/prolonging by application of a negative/positive amplitude pulse or cathodic/anodic stimulus) involved the employment of electrical stimuli delivered during the absolute refractory period (Brunckhorst C B, Shemer I, Mika Y, et al. Cardiac contractility modulation by non-excitatory currents: studies in isolated cardiac muscle. *Eur J Heart Fail.* January 2006; 8(1):7-15; Augello G, Santinelli V, Vicedomini G, et al. Cardiac contractility modulation by non-excitatory electrical currents. The new frontier for electrical therapy of heart failure. *Ital Heart J.* June 2004; 5 Suppl 6:68S-75S; Pappone C, Augello G, Rosanio S, et al. First human chronic experience with cardiac contractility modulation by nonexcitatory electrical currents for treating systolic heart failure: mid-term safety and efficacy results from a multicenter study. *J Cardiovasc Electrophysiol.* April 2004; 15(4):418-427; Pappone C, Rosanio S, Burkhoff D, et al. Cardiac contractility modulation by electric currents applied during the refractory period in patients with heart failure secondary to ischemic or idiopathic dilated cardiomyopathy. *Am J Cardiol.* Dec. 15, 2002; 90(12):1307-1313; Pappone C, Vicedomini G, Salvati A, et al. Electrical modulation of cardiac contractility: clinical aspects in congestive heart failure. *Heart Fail Rev.* January 2001; 6(1):55-60).

SUMMARY OF THE INVENTION

The present invention includes a method of preventing heart rhythm disturbances comprising: (i) detecting (and optionally recording) cardiac electrical activity (ii) measuring beat-to-beat variability in the cardiac electrical activity and (iii) using the beat-to-beat variability to control therapy to reduce the likelihood of heart rhythm disturbances. In certain embodiments, the beat-to-beat variability comprises repolarization alternans and/or heart rate variability.

The therapy comprises the delivery of one or more chemical substances and/or the delivery of electrical impulses to the heart. The electrical impulses may be controlled to alter the variability in the inter-beat interval or the diastolic interval.

A number of heart rhythm disturbances, including but not limited to tachyarrhythmias and bradyarrhythmias, are preventable by use of the invention.

In certain preferred embodiments, the electrical activity of the heart is recorded from a passive electrode within the heart. In another preferred embodiment, the electrical activity of the heart is recorded from a multiplicity of passive electrodes within or close to the heart. In another preferred embodiment, the electrical activity of the heart is recorded from a passive electrode in the coronary sinus, which is capable of recording unipolar (near-field) and bipolar (far-field, reference electrode the ICD can) electrograms.

In another preferred embodiment a combination of electrocardiographic and hemodynamic criteria will be employed to trigger therapy. In such an embodiment the hemodynamic criterion includes recording the beat-to-beat variability in the morphology of arterial blood pressure and establishing thresholds that would trigger therapy. In another embodiment the hemodynamic criterion includes recording or estimating the instantaneous lung volume and establishing thresholds that would trigger therapy.

In another embodiment, the measuring step is performed in an implanted device. In yet another embodiment, the therapy is delivered by an implanted device. The implanted device optionally serves as a cardiac pacemaker or a cardiac cardioverter/defibrillator.

In another embodiment such device can contain a reservoir of chemical substance and delivery means, and deliver the compound to the patient at the appropriate times and dosages. This chemical substance may be a pharmacological agent that reduces the likelihood of a heart rhythm disturbance from occurring. The substance may be delivered into the blood stream or directly into the heart.

In another embodiment, the implantable device has means for generating electrical stimulating pulses of specified increasing energies and applying the pulses to body tissue at specified adjusted times appropriate for preventing the heart rhythm disturbance.

In a further embodiment, the measuring step further comprises identifying periods when there is an increased probability that a heart rhythm disturbance may occur. Periods of increased susceptibility to life threatening arrhythmias are characterized by increased levels of repolarization alternans or reduced heart rate variability. In these identified periods, therapy may be delivered.

The present invention will reduce the morbidity and mortality resulting from heart rhythm disturbances and the pain and complications associated with the termination of heart rhythm disturbances, in certain embodiments, by administering low energy electrical shocks. The present invention will also reduce the morbidity and mortality resulting from heart rhythm disturbances, by administering high energy electrical shocks such as occurs when an implanted cardioverter defibrillator (ICD) discharges to terminate ventricular tachycardia or fibrillation.

Application of early therapy by means of this invention utilizing an ICD will provide a significant improvement in preventing SCD. Currently, state of the art ICDs identify an abnormal heart rhythm based on the detection of its rate and morphology. However, failure or delay in detecting ventricular tachycardia or ventricular fibrillation are common. False detection of ventricular tachycardia or ventricular fibrillation is also a concern. In addition, the implications of an intervention after the development of an abnormal rhythm are not exactly known. Energy delivery in the myocardium, even if it succeeds to revert the heart rhythm to normal, is not an unharmful intervention either in short or long term of the cardiac function. Usually, an increase in energy delivered is required in repetitive shocks and as a result a possible accumulative damage in the cardiac tissue occurs. Moreover, depending on the type of the abnormal heart rhythm, an ICD may not succeed to lead the heart back to a normal rhythm. The above methodology may not to be applied only in an ICD but also in a cardiac pacemaker. As used herein, the term implantable device (ID) refers to either an ICD or a cardiac pacemaker.

In the setting of alternans, either moderately prolonging or shortening the QT interval can be beneficial not only in suppressing/terminating RA but also in preventing VT/VF. Nonexcitatory current will be applied during the absolute refractory period to modulate the local APD and consequently the QT interval. Thus, application of pacing is expected to affect both the dynamics of the APD and the scar tissue core, in such a way that it provokes bi-directional block and termination of reentry that may underlie repolarization alternans (RA) and susceptibility to VT/VF.

BRIEF DESCRIPTION OF THE DRAWING

Embodiments of the present invention are explained in greater detail below on the basis of FIGS. 1a through 5 of the attached drawing, where:

FIG. 5 is an illustration of an ICD having drug ports for therapy delivery in accordance with certain embodiments of the present invention.

DETAILED DESCRIPTION OF CERTAIN PREFERRED EMBODIMENTS OF THE INVENTION

Figure 1A:
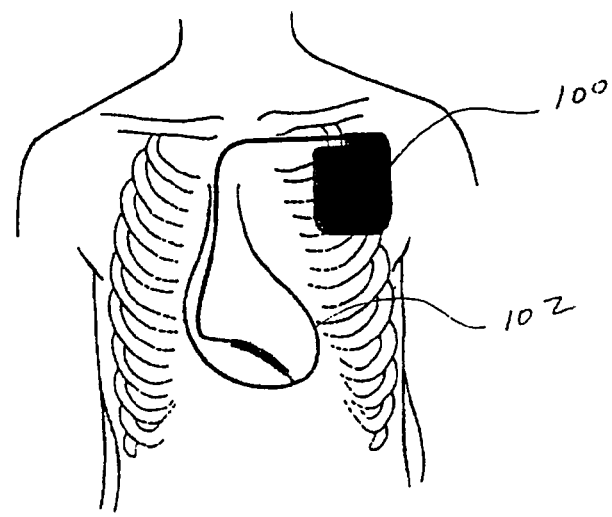
FIGS. 1a, 1b are front and side illustrations of a human torso within which is depicted an implantable cardioverter defibrillator.
Figure 1B:
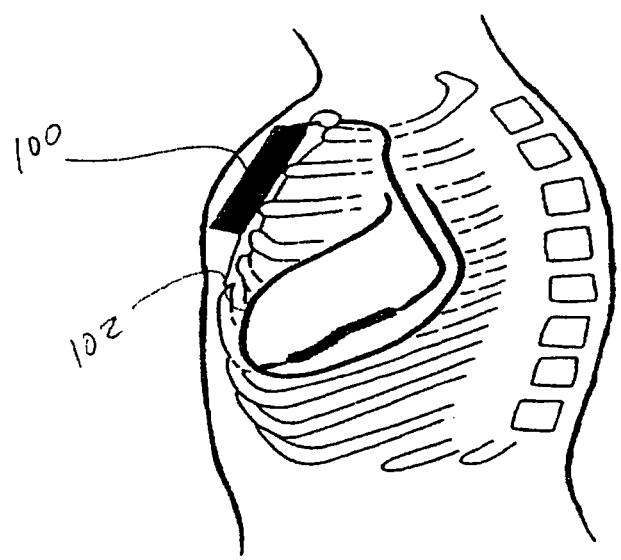
Figure 2:
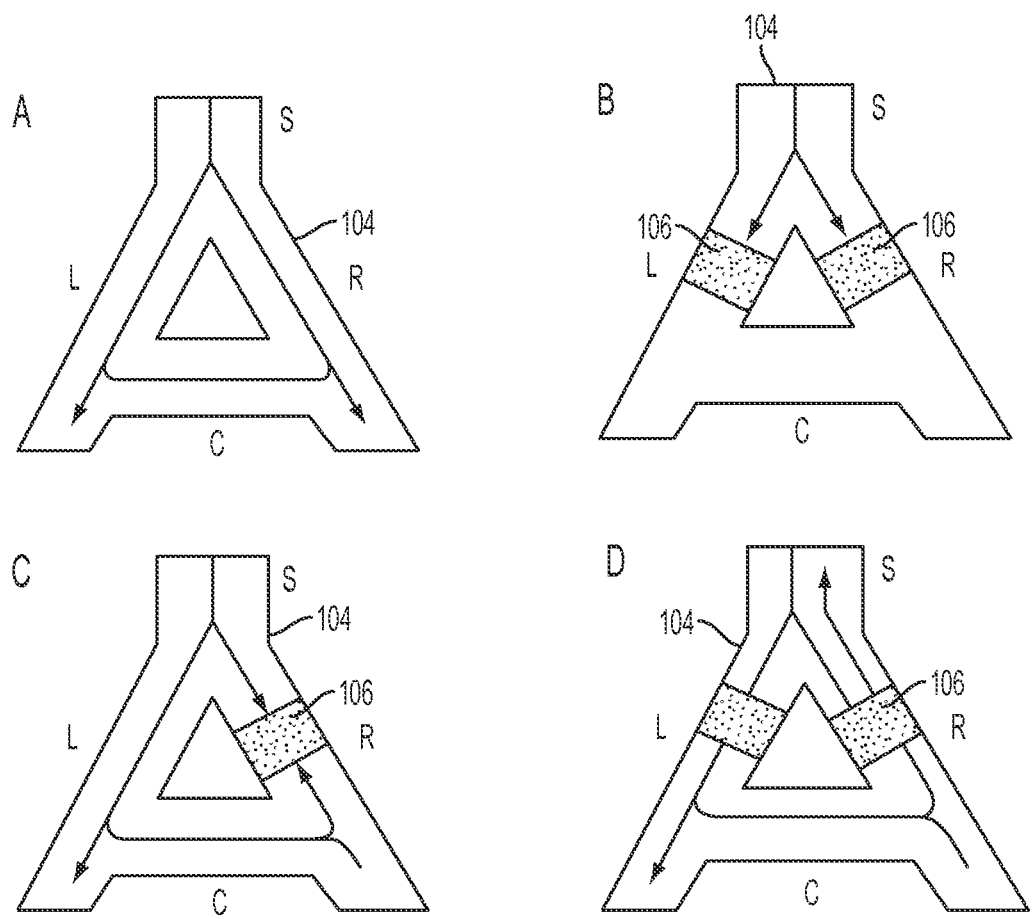
FIGS. 2a-2d are illustrations of the role of a unidirectional block in reentry (the figure is adapted from "Cardiovascular Physiology", by R. M. Berne and M. N. Levy)
Figure 3:
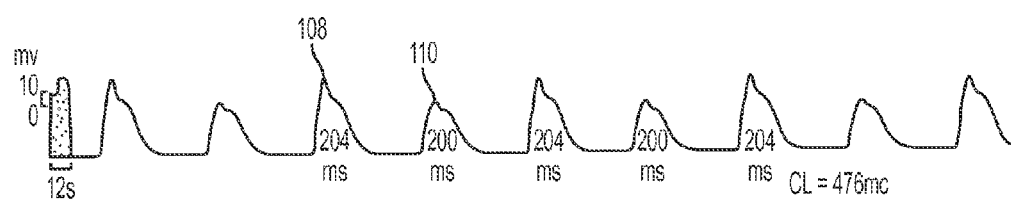
FIG. 3 is an illustration of monophasic action potentials during atrial pacing-alternans after 50 sec of graft occlusion and the progressive development is shown, while interbeat duration shows only a small variation, amplitude changes are striking (adapted from Sutton, PMI, et al. *Eur. Heart J.* 1991; 12:70)
Figure 4:
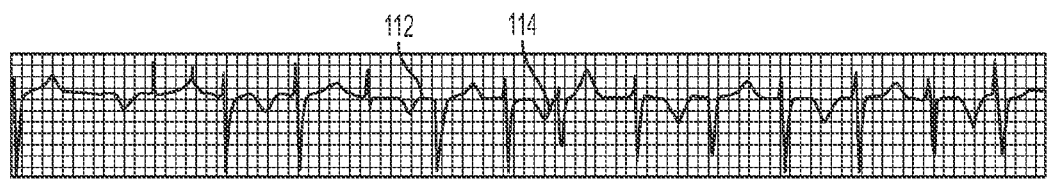
FIG. 4 is a reproduction of a clinical tracing illustrating isolated alternation of the T-wave—the QRS complex is normal in duration, with alternation of polarity of the T-wave (adapted from "Heart Disease", A textbook of cardiovascular medicine, by Eugene Braunwald)

Preferred embodiments of the invention will now be described with reference to the accompanying figures.

A preferred embodiment for this invention involves an apparatus for and method of preventing heart rhythm disturbances that involves detecting (and optionally recording) cardiac electrical activity from electrodes placed in or on the patient's body proximate the patient's heart. The cardiac electrical activity is monitored and beat-to-beat variability in the cardiac electrical activity is measured. A variety of algorithms have been described in the art for measuring variability, including several co-developed by the applicants and described in the following references, which, like all the articles mention in this application, are incorporated herein by reference: Rosenbaum, D S, et al., "Electrical alternans and vulnerability to ventricular arrhythmias", *N Engl J Med.* 1994; 330:235-41; Adam, D R, et al., "Fluctuations in T-wave morphology and susceptibility to ventricular fibrillation", *J Electrocardiol.* 1984; 17:209-18; Smith J M, et al., "Electrical alternans and cardiac electrical instability", *Circulation,* 1988; 77:110-21; Chon, et al. "Detection of "noisy" chaos in a time series", *Methods Inf Med.* 1997; 36:294-7; and Armoundas, et al. "A stochastic nonlinear autoregressive algorithm reflects nonlinear dynamics of heart-rate fluctuations" *Ann. Biomed. Eng.* 2002; 30:192-201. The measured beat-to-beat variability in the heart's electrical activity provides information on the likelihood of heart rhythm disturbances occurring. The invention uses this information to control therapy to prevent the heart rhythm disturbance from occurring.

In certain preferred embodiments, the beat-to-beat variability is repolarization alternans. As discussed above, repolarization alternans has been well established as a predictor of the development of ventricular arrhythmias. In a method in accordance with the present invention, the level of repolarization alternans can be quantified by means well known in the art, such as measurement of the alternans voltage and measurement of the alternans ratio in one or more electrocardiographic leads. Threshold values of these parameters can be established such as 1.9 microvolts for the alternans voltage and a value of 3.0 for the alternans ratio. When the level of repolarization alternans exceeds a threshold value over some period of time (such as one minute) therapy is delivered to suppress the repolarization alternans and thus reduce the likelihood that a heart rhythm disturbance will occur. Repolarization alternans can be reliably estimated by analysis of approximately 128 beats. Thus, in about a minute or so (assuming a rate of 105-110 beats/min) the number of beats needed in the estimation will have been detected and/or recorded. As previously defined, repolarization alternans as used herein includes any change in the morphology of the T-wave or ST segment of the electrocardiogram on occurring on an every other beat basis. In other embodiments, the beat-to-beat variability in the cardiac electrical activity that is measured is heart rate variability. As discussed above and in Armoundas et al. "A stochastic nonlinear autoregressive algorithm reflects nonlinear dynamics of heart-rate fluctuations", *Ann. Biomed. Eng.* 2002; 30:192-201, reduced heart rate variability is a well known predictor of the development of ventricular arrhythmias. (See also Chon, *Methods Inf Med.* 1997; 36:294-7.) For example, a threshold value of heart variability may be established, such as the Standard Deviation of Normal to Normal RR intervals measure of heart rate variability being equal to 60 milliseconds. When the heart rate variability is less than the threshold value for some period of time (e.g., one minute) then therapy is delivered to increase the heart rate variability and thus reduce the likelihood that a heart rhythm disturbance will occur.

The invention provides control over the delivery of one or more therapeutic chemical substances. The chemical substance may be a pharmacological agent that reduces the likelihood of a heart rhythm disturbance from occurring, such as a class III antiarrhythmic drug, beta-blocker, or ace inhibitor. The delivery time and dosages are determined on a case-by-case basis based upon a number of patient factors. The substance may be delivered into the blood stream or directly into the heart.

In alternative embodiments, the controlled therapy comprises the delivery of electrical impulses to the heart through electrodes in or on the heart. The electrical impulses may cause the excitation of the cardiac tissue and thus pace the heart. The energy of these impulses is far less than the energy associated with delivery of a defibrillation shock to terminate ventricular fibrillation. Thus these impulses do not cause damage to the heart tissue. In one preferred embodiment the electrical impulses may be delivered at varying inter-impulse intervals so as to increase the level of heart rate variability. For example, the inter-impulse intervals may have a mean of 600 milliseconds and a standard deviation of 120 milliseconds. In general, the mean inter-impulse interval needs to be chosen small enough so that most of the heart beats result from the applied impulses and not from spontaneous cardiac electrical activity. The variable inter-beat intervals will also cause the diastolic intervals associated with cardiac electrical activity in the heart's ventricles to vary. Since the ST and T-wave morphology also depends on the duration of the preceding diastolic interval, the variability in the timing of the electrical impulses will also cause increased variability in ST and T-wave morphology and thus tend to suppress repolarization alternans.

The delivered therapeutic electrical stimulus preferably has a minimum energy level similar to that delivered by pacemakers (pacing pulse), and a maximum energy level similar to that delivered by defibrillators (defibrillation shock) commonly known to those skilled in the field. The therapeutic electrical stimulus should be preferably delivered outside the vulnerable window wherein ventricular fibrillation may be induced.

In another preferred embodiment, when there is alternation in the Beat Duration (duration of time from the beginning of depolarization to the end of repolarization), the electrical impulse is delivered at a time interval after the end of repolarization in the beats with the shorter Beat Duration. This time interval is longer than the diastolic interval that follows the beats with the longer Beat Duration but shorter than the diastolic interval that follows the beats with the shorter Beat Duration. Among the heart rhythm disturbances that are being prevented are tachyarrhythmias and bradyarrhythmias. Tachyarrhythmias that are of particularly severe risk to a patient are ventricular tachycardia or ventricular fibrillation. Both of these tachyarrhythmias may be fatal if untreated.

In preferred embodiments the electrical activity of the heart is detected and recorded from a passive electrode within the heart. Such electrodes may be placed in the atrium, ventricle or coronary sinus of the heart. In another preferred embodiment, the passive electrode in the coronary sinus is capable of recording both unipolar (near-field) and bipolar (far-field, reference electrode the ICD can) electrograms. In another preferred embodiment, the electrical activity of the heart is recorded simultaneously from a multiplicity of passive electrodes within or close to the heart. In another preferred embodiment, the electrical activity of the heart recorded simultaneously from a multiplicity of passive electrodes is optimally used to determine when to trigger therapy.

In another preferred embodiment a combination of electrocardiographic and hemodynamic criteria will be employed to trigger therapy. In such an embodiment the hemodynamic criterion includes recording the beat-to-beat variability in the morphology of arterial blood pressure and establishing thresholds that would trigger therapy. In another embodiment the hemodynamic criterion includes recording or estimating the instantaneous lung volume and establishing thresholds that would trigger therapy.

The beat-to-beat variability measurement may be performed in an implanted device such as an implantable cardioverter defibrillator or cardiac pacemaker. Such devices contain miniature microprocessors capable of performing the computations necessary for the measurement. As discussed above, a variety of algorithms for computing the variability based upon repolarization alternans or heart rate variability are known to those skilled in the field, and several are described in the references cited and incorporated in this application. These devices can both implement the method of this invention and serve also as a cardioverter defibrillator or pacemaker.

The therapy in certain embodiments is also delivered by the implanted device. For example the implantable device can incorporate the means for generating electrical stimulating pulses of specified energies and applying the pulses to body tissue at specified times, and deliver the impulses used for pacing the heart at the appropriate times and energy levels that are selected as described above. In another preferred embodiment such devices can contain a reservoir of chemical compound and delivery means, and deliver the compound to the patient at the appropriate times and dosages whose selection is likewise described above. An ICD 116 equipped with drug ports is illustrated in FIG. 5 as an exemplary embodiment of the present invention.

In a preferred embodiment the measured beat-to-beat variability in cardiac electrical activity (i.e. instantaneous measurement to of of repolarization alternans and/or heart rate variability) to identify periods when there is an increased probability that a heart rhythm disturbance may occur will be compared to a baseline level of repolarization alternans measured prior to the patient's discharge from the hospital.

In a preferred embodiment, application of adaptive pacing will be used to alter the repolarization duration in order to suppress/terminate RA. In another preferred embodiment, adaptive pacing will be employed in such way that electrical stimuli will be applied on alternate beats during alternans.

In another preferred embodiment, non-excitatory current will be applied during the absolute refractory period, to modulate the local APD and consequently the QT interval. In a preferred embodiment the following parameters of the current pulses will be altered to confirm suppression/termination of RA, the: (i) amplitude, (ii) duration, and (iii) delay from the R-wave.

In a preferred embodiment monophasic square-wave current pulses (i) with peak amplitudes ranging between 1 and 20 mA in incremental steps of 1 mA (corresponding to an approximate range of 0.5 to 10 V, for ~500Ω impedance), (ii) with duration ranging from 10 to 50 msec, in incremental steps of 2 msec, and (iii) that are delivered 10 to 50 msec in incremental steps of 2 msec after the R-wave, will be applied on alternate beats.

In a preferred embodiment current pulses will be applied on a beat-to-beat basis during alternans by attempting to prolong (by applying a positive amplitude pulse or anodic stimulus) or shorten (by applying a negative amplitude pulse or cathodic stimulus) the QT interval, on either the short (in an attempt to prolong it) or the long (in an attempt to shorten it) beats on alternate beats.

Other embodiments of the invention will be apparent to those skilled in the art from a consideration of the specification or practice of the invention disclosed herein. It is intended that the specification and examples herein be considered as exemplary only, with the true scope and spirit of the invention being indicated by the following claims.

The contents of all of the literature and other references cited throughout this specification are incorporated herein by reference in their entirety.

We claim:

1. A system for preventing a heart rhythm disturbance comprising:
   a detector configured to detect cardiac electrical activity;
   an analyzer configured to analyze the cardiac electrical activity to measure beat-to-beat variability in the morphology of electrocardiographic waveforms;
   wherein the system is configured to (a) determine whether the measured beat-to-beat variability exceeds a threshold used to trigger therapy and (b) deliver electrical impulses during a refractory period when the threshold is exceeded.

2. The system of claim 1, wherein the beat-to-beat variability is repolarization alternans.

3. The system of claim 1, wherein the system is configured to detect and analyze beat-to-beat variability in arterial blood pressure.

4. The system of claim 1, wherein the system is configured to detect and analyze beat-to-beat variability in instantaneous lung volume.

5. The system of claim 1, wherein the system is configured to prevent a tachyarrhythmia.

6. The system of claim 1, wherein the system is configured to prevent a bradyarrhythmia.

7. The system of claim 1, wherein the detector comprises at least one passive electrode configured to be placed inside the body in the vicinity of the heart of a patient.

8. The system of claim 1, wherein the detector comprises at least one passive electrode configured to be positioned within the heart of a patient.

9. The system of claim 1 further comprising a device configured to be implanted into a patient.

10. The system of claim 9 wherein the device incorporates the detector and/or incorporates the analyzer and/or is able to deliver the electrical impulses.

11. The system of claim 9, wherein the device is configured to function as at least one of (a) a cardiac pacemaker and (b) a cardiac cardioverter/defibrillator.

12. The system of claim 9, wherein the device includes means for generating electrical stimulating pulses of specified energies and applying the pulses to body tissue at specified times.

13. The system of claim 9, wherein the device includes means for generating electrical stimulating pulses of specified amplitudes and durations and applying the pulses to body tissue at specified times.

14. The system of claim 1, wherein the system is configured to deliver electrical impulses to reduce repolarization alternans.

15. The system of claim 1, wherein the system is configured to deliver the electrical impulses during absolute refractory period on alternate beats.

16. The system of claim 1, wherein the system is configured to deliver the electrical impulses during absolute refractory period of each beat.

17. The system of claim 1, wherein the system is configured to deliver electrical impulses that alternate in polarity in successive beats.

18. The system of claim 1 wherein the refractory period is the absolute refractory period.

19. A system for preventing a heart rhythm disturbance comprising:
    electrode means for detecting cardiac electrical activity;
    means for analyzing the cardiac electrical activity to measure beat-to-beat variability in the morphology of electrocardiographic waveforms;
    means for determining whether the measured beat-to-beat variability exceeds a threshold used to trigger therapy; and
    means for delivering electrical impulses during a refractory period when the threshold is exceeded.

* * * * *